United States Patent [19]

Tao et al.

[11] Patent Number: 4,492,637
[45] Date of Patent: Jan. 8, 1985

[54] WATER SEPARATION PROCESS

[75] Inventors: Luh C. Tao, Lincoln, Nebr.; James W. Blease, Rochester, N.Y.

[73] Assignee: The Board of Regents of the University of Nebraska, Lincoln, Nebr.

[21] Appl. No.: 554,947

[22] Filed: Nov. 25, 1983

[51] Int. Cl.$^3$ .............................................. B01D 9/02
[52] U.S. Cl. .................................... 210/711; 210/712; 210/713; 210/714; 210/737; 210/774; 568/916; 568/920
[58] Field of Search ........ 159/45, DIG. 20, DIG. 23, 159/DIG. 38; 210/175, 194, 198, 633, 673, 676, 677, 710, 711, 712, 713, 714, 737, 766, 770, 771, 774; 423/192, 551, 553, 659; 62/533; 568/916, 920

[56] References Cited

U.S. PATENT DOCUMENTS

| | | | |
|---|---|---|---|
| 2,007,956 | 7/1935 | Davis et al. | 159/45 |
| 2,904,511 | 9/1959 | Donath | 210/194 |
| 2,974,102 | 3/1961 | Williams | 210/711 |
| 3,148,143 | 9/1964 | Donath | 210/711 |
| 3,415,747 | 12/1968 | Glew | 210/737 |
| 3,974,039 | 8/1976 | Frohner et al. | 210/714 |

Primary Examiner—Ivars Cintins
Assistant Examiner—W. Gary Jones
Attorney, Agent, or Firm—Vincent L. Carney

[57] ABSTRACT

To reduce the amount of high quality energy utilized in removing water from a dilute ethanol solution, a two-stage process is used. The first stage removes eighty-five percent of the water using a low temperature apparatus and process and the remainder of the energy is removed by any of the other conventional processes. In the first stage, anhydrous sodium sulfate is dissolved in a dilute aqueous solution of 10 weight percent alcohol at approximately thirty degrees centigrade. The solution is cooled to approximately twenty degrees centigrade, at which temperature decahydrate crystals of sodium sulfate precipitate from the solution are removed. The solution is increased to a value in excess of 45% of alcohol which requires removal of approximately 82 percent of the water in the form of crystals. The crystals are dried to the anhydrous state at substantially room temperature and reused.

9 Claims, 2 Drawing Figures

WATER SEPARATION PROCESS

BACKGROUND OF THE INVENTION

This invention relates to the separation of water from solutions of organic compounds.

It is known to separate water from organic compounds in more than one step. For example, in some processes, water is separated from an ethanol solution to provide a higher concentration of ethanol than that created by fermentation of sugars in the initial culture and still further water is removed in successive steps.

In the prior art, multiple stage techniques for separating water from an organic material, high quality energy approaches are used to separate large amounts of water in a first step and then smaller amounts of water are separated by other techniques. For example, in one process, most of the water in a solution of alcohol and water formed by fermentation is removed by fractional distillation and the last fraction is removed by using a chemical such as benzine to provide anhydrous ethanol. It is also known to remove the last small traces of moisture by other dehydrating materials such as dehydrating salts and the like.

The prior art methods have the disadvantage of using large amounts of high quality energy to remove most of the water.

SUMMARY OF THE INVENTION

Accordingly, it is an object of the invention to provide a novel process for separating water from an organic compound.

It is a further object of the invention to provide novel apparatus for separating water from an organic compound.

It is a still further object of the invention to provide a technique which uses primarily low-quality energy to remove the bulk of the water from a dilute aqueous solution of an organic compound.

It is a still further object of the invention to provide a novel technique for removing between 40 percent and 85 percent of the water from a 10 percent ethanol solution as the first stage in a multi-stage process leading to relatively dry ethanol.

In accordance with the above and further objects of the invention, between 40 percent and 85 percent of the water in a dilute solution of organic compound is removed in a first stage at approximately room temperature using materials which may be renewed without excessive high quality energy expenditure at approximately room temperature. Further water may be removed in further steps of a multiple step process leading to relatively dry organic material.

Advantageously, anhydrous sodium sulfate is dissolved in the solution to be dried at approximately 30 degrees centrigrade. The solution is then cooled to approximately 20 degrees centigrade, resulting in a precipitate of hydrated sodium sulfate which may be separated from the remaining liquid.

With this process, more than 85 percent of the water can be removed from the organic compound using inexpensive, low-grade energy sources. The crystalline hydrated sodium sulfate is regenerated by permitting it to dry at room temperature in a gentle breeze for reuse. This process is particularly advantageous in removing large quantities of the water in a low concentration ethanol solution such as a 10 percent solution which may be obtained during fermentation. The ethanol may then be further dried to anhydrous alcohol by further conventional stages.

The technique of this invention has the advantage of removing large quantities of water with very little high-quality energy thus resulting in cost saving of energy.

SUMMARY OF THE DRAWINGS

The above noted and other features of the invention will be better understood from the following detailed description when considered with reference to the accompanying drawings in which.

SPECIFIC DESCRIPTION

Broadly, water is removed from a dilute solution of an organic substance using only low-quality energy with the separation being effected at close to room temperature and between 40 and 85 percent of the water being removed with this low-quality temperature. At later stages, more water is removed but usually using higher quality energy.

More specifically, the bulk of the water is removed by inserting in the solution of water and an organic material, a hydrating material which hydrates at low temperature and which can easily be separated after it has bound substantial amounts of water to it. This is a substance having sufficiently high vapor pressure in the hydrated state so that it may be regenerated using low-quality energy. It should be returnable to a dry or anhydrous state at substantially room temperature.

Advantageously, the ratio of molecular weight of the hydrated substance to the molecular weight of the anhydrous state of the substance to be used should be very high and substantially in a range between one-to-one and three-to-one. Preferably it should be nontoxic and inexpensive.

Still more specifically, the process includes four steps comprising: (1) the insertion of an anhydrous material into the water solution; (2) the hydrating of that material; (3) the removal of the hydrated material; and (4) the regeneration of the hydrated material to the anhydrous state with all of the four steps taking place close to room temperature.

Preferably, the material in its anhydrous form is inserted into the solution and dissolved at a slightly elevated temperature of no more than 15 degrees centigrade above room temperature and then crystallized at substantially room temperature or slightly lower temperature than room temperature, with the regeneration taking place at close to room temperature or slightly above room temperature. A suitable material which has a ratio of molecular weights of approximately two-to-one between its hydrated state and anhydrous state and in which all four steps may take place at close to room temperature is sodium sulfate.

Figure 1:
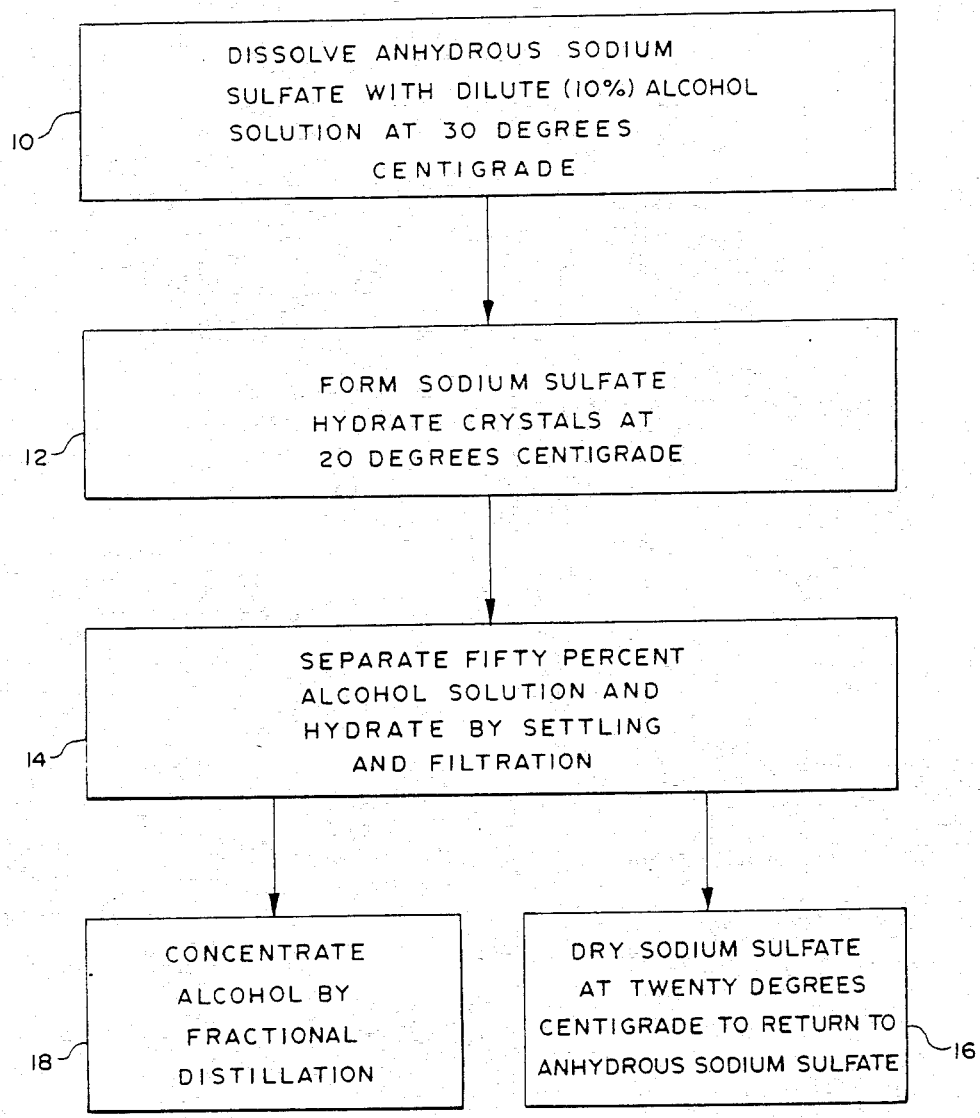
FIG. 1 is a flow diagram of a process for removing the largest part of the water from a solution of an organic compound in accordance with an embodiment of the invention.

In FIG. 1, there is shown a flow diagram of a process for concentrating a 10 percent solution of ethanol to a 50 percent solution of ethanol using primarily low-quality energy and performing the operations at substantially room temperature including: (1) the step 10 of dissolving anhydrous sodium sulfate into the 10 percent ethanol solution and dissolving the sodium sulfate at thirty degrees centigrade, a suitable temperature for the anhydrous sodium sulfate to go into solution; (2) the step 12 of forming sodium sulfate hydrate crystals by cooling the solution to twenty degrees centigrade so that the crystals are formed and precipitate out of the solution; (3) the step 14 of separating the 50 percent ethanol solution and the sodium sulfate hydrate crystals by filtering the crystals from the solution; (4) the step 16 of drying the sodium sulfate hydrate crystals at room temperature with a slight breeze so that it returns to the anhydrous state for reuse in step 10; and (5) the step 18 of concentrating the alcohol by fractional distillation or other means.

When starting with a dilute solution which commercially must be concentrated, use of high quality energy is minimized in the process of separating water from the basic organic material, such as for example, separation of ethanol formed in a process of fermentation which leaves it a very diluted solution. The conventional method of removing the water involves the use of high quality energy in the first step which removes most of the water coupled by further use of energy necessary to remove the last quantities of water. This invention removes most of the water using low-grade energy and completes the process using higher grade energy, if necessary.

Sodium sulfate was selected for removal of the water for several reasons such as: (1) it is nontoxic; (2) it is inexpensive; (3) its anhydrous form is soluble in a dilute solution of alcohol; (4) it forms a decahydrate in solution which has a molecular weight that is approximately double that of the molecular weight of the anhydrous sodium sulfate; (5) its saturation level is high enough to remove water and to result in a concentrated alcohol solution; (6) it goes into solution in a suitable quantity at a relatively low temperature, which is thirty degrees, thus enabling solar energy or other low-quality energy or only small amounts of high-quality energy to be used to bring it into solution; (7) in the hydrate crystal form, its vapor pressure is sufficiently high so that it returns to the anhydrous form at a low temperature; (8) it crystallizes out at approximately room temperature so that it may be easily removed; and (9) it is relatively easy to handle and can be cleaned from containers or the like with ordinary water.

In the preferred embodiment, a saturated solution of sodium sulfate is prepared in a single step to remove the bulk of the water. Other salts would have different saturation and it would be possible, by using a temperature higher than thirty degrees centigrade, to increase the amount of sodium sulfate in the saturated solution and thus remove more water but at the expense of more energy. Similarly, successive steps on the same dilute solution could be used so that: (1) the bulk of the moisture is removed by one sequence of dissolving anhydrous sodium sulfate, crystallizing it and separating the crystals; and (2) further water removed by subsequent steps of dissolving new anhydrous sodium sulfate at thirty degrees and crystallizing it out at twenty degrees.

While there are advantages to sodium sulfate, other salts may be used which remove more or less water. The procedure is efficient because a large portion of the water may be economically removed through the use of only small amounts of high-quality energy by a single step utilizing a salt which removes most of the water in that single step.

The removal of the hydrate is accomplished at twenty degrees centigrade in the preferred embodiment by simply cooling the solution down by using inexpensive cooling water or the like. However, certain crystallization techniques such as seeding with borax or other methods are known to increase the crystallization effect and may be used. Similarly, it is possible that the hydrate may be separated by other techniques involving differences in the density of the hydrate and the solution or the like.

While the regeneration of the sodium sulfate decahydrate to its anhydrous form is accomplished at room temperature with a minimum amount of high quality energy, the process may be speeded up by slightly elevating the temperature or by stirring or the like. The specific method to be used is tailored to the available sources of low-cost energy.

The inventive process does not contemplate any specific technique for removal of the rest of the water in the alcohol solution if further dehydration is to be accomplished. It may be by fractional distillation or by extractive distillation known in the art or by any other suitable combination of methods. Under some circumstances, it may even be desirable to repeat a treatment with sodium sulfate to remove further water.

Figure 2:
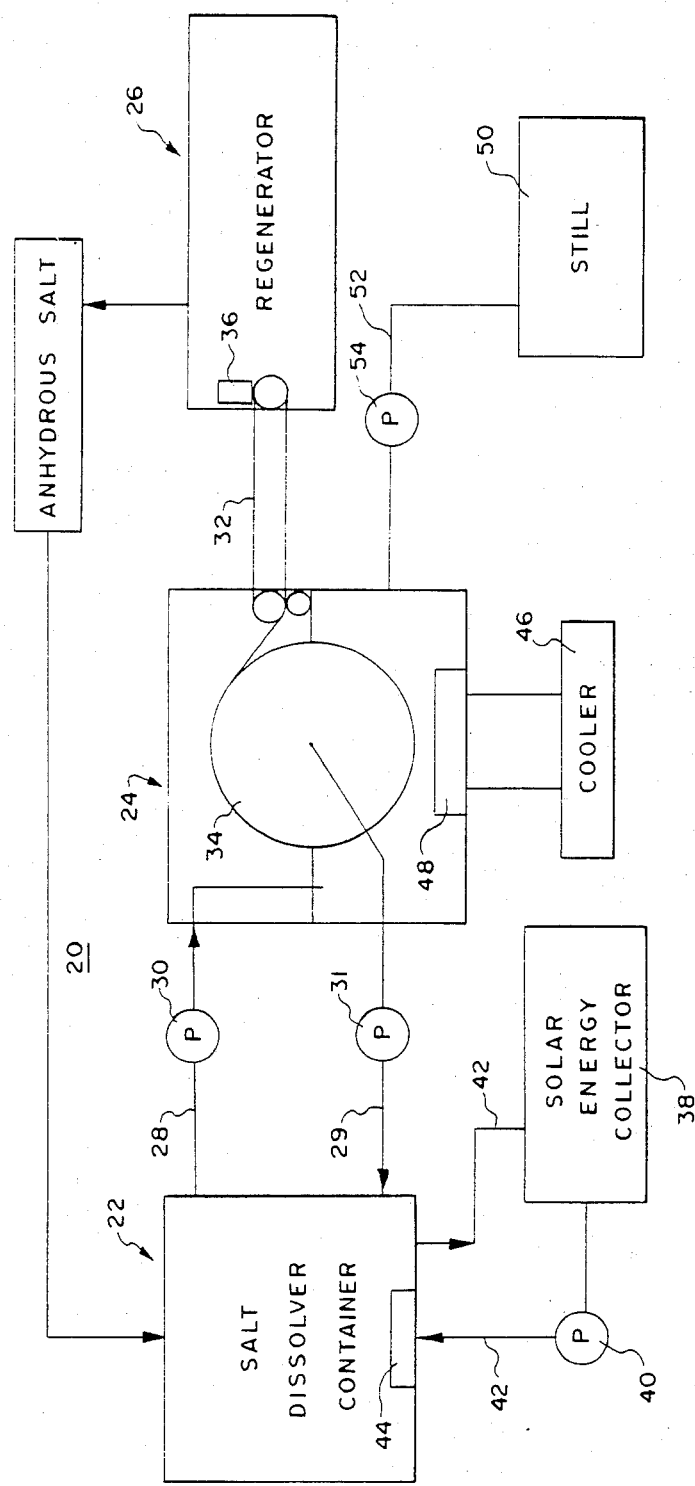
FIG. 2 is a simplified block diagram of an embodiment of the invention.

In FIG. 2 there is shown a schematic system 20 for separating water from an organic compound having a salt solution container 22, a separation container 24 and a regenerator 26, connected together to: (1) dissolve an anhydrous salt in the organic solution; (2) pump it into the separation container 24; (3) separate hydrated salt from it; and (4) regenerate the hydrated salt in the regenerator 26.

To pump the organic solution from the salt solution container 22 between the separation container 24 and the salt solution container 22, the salt solution container 22 communicates with the separation container 24 through a conduit 28 having a pump 30 and the conduit 29 having a pump 31 arranged to pump the solutions from one container to another. While in the embodiment of FIG. 2, conduits and a pump are shown to move the fluid from one container to another, any suitable technique may be used including gravity flow in one direction. Moreover, it is possible to utilize only one container to both dissolve the anhydrous salt and to precipitate the hydrate therefrom to separate water from the organic solution.

To apply and return the solution to a salt solution container 22 from the separating container 24, the first conduit 28 is above the second conduit 29 which communicates near the bottom of the salt solution container 22 and the separation container 24. Fluid is pumped through conduit 29 by the pump 31. If the two containers are substantially horizontal, only the pump 31 is necessary since it will increase the height of the fluid in the salt solution container 22 so that it flows by gravity or siphoning through the conduit 28. The pump or pumps are intended to recirculate the solution at a relatively low rate of flow so that fluid entering separation container 24 is not a supersaturated solution.

To separate the hydrated salt from the organic solution, a rotatable filter 32 is mounted partly within the separation container 24. The rotatable filter 34 moves precipitate from separation container 24 to a conveyer 32 and into the regenerator 26. While a specific kind of movable filter is described in connection with the embodiment of FIG. 2, any type of filtrate separation device may be used or any other conventional method for separating the hydrate from the organic solution.

In the embodiment of FIG. 2, the salt solution container 22 is intended to dissolve anhydrous sodium sulfate in a dilute solution of ethanol which takes place with very low enthalpy of the solution. For example, a satisfactory amount of sodium sulfate may be dissolved at approximately thirty degrees centigrade. Thus, even if high-quality energy were used, a substantial amount would not be required.

To heat the solution in the salt dissolver container 22 to a temperature selected for the dissolving of the salt, the embodiment of FIG. 2 contains a solar collector 38, a pump 40, conduits 42 and a radiator 44. The solar collector 38 heats a fluid which is circulated through the conduit 42 by the pump 40. The conduit circulates within the radiator 44 which is in juxtaposition with the solution within the salt solution container 22 to heat the solution, using primarily principally low-cost, low-quality energy obtained from the solar collector 38.

While a solar collector 38 is disclosed in FIG. 2 to provide a source of low-quality energy, any other heating source may be used. For example, a waste gas heat exchanger may be used to raise the temperature, particularly where the temperature need only be increased by a small amount.

To aid in precipitation of the sodium sulfate hydrate crystals, the embodiment of FIG. 2 includes a cooler 46 mounted to circulate cooled fluid through a radiator 48 to remove heat from the liquid within the separation container 24. With this mechanism, any heat sink may be used to provide the desired cooling differential. For example, cool water from a flowing stream of water circulated through an immersed coil or the like would be suitable.

While a cooling system is disclosed in connection with the separation container 24 to cause precipitation of the filtrate, any other appropriate system may be used. For example, in the case of sodium sulfate hydrate, crystals are formed quite well at room temperature. Moreover, seeding is known to cause precipitation. Other precipitation conditions may be desirable for other salts.

To regenerate the crystals, the regenerator 26 may simply be an open container which provides slight stirring action or breeze such as by a fan to the sodium sulfate decahydrate crystals. Thus, no substantial amount of high-quality energy is needed. If some slight heat is desired, heat preferably from a low-quality energy source such as a solar collector 38 or the like, may be used to speed the process. Moreover, the regenerator 26 for other salts may be provided under still different conditions.

After the bulk of the water has been separated from the solution, further separation may take place in a still 50 to which the fluid may be pumped through a conduit 52 with an appropriate pump 54.

Usually several hours of circulation are necessary to reduce a sufficient amount of the water before the pump 54 pumps the fluid from the container 24 to the still 50 but the time is determined for each situation. In the still 50 further concentration takes place. Generally, the circulation may continue in the first stage to whatever concentration is necessary but the period of time necessary for the run becomes excessively long as the concentration of alcohol approaches 50 percent.

While in the embodiment of FIG. 2, fractional distillation is disclosed by means of a still, any other means for separating further water may be utilized instead or for some applications it may be unnecessary to separate further water.

The following non-limitative examples further illustrate the invention:

In each case: (1) a dilute solution of ethanol and water was circulated between two containers such as those shown at 22 and 24 in FIG. 2, with the solution container 22 being maintained at one temperature and the separation container 24 at another temperature; (2) an excess of anhydrous sodium sulfate was placed in solution container 22 and the solution to be concentrated was poured into solution container 22 and flowed into separation container 24 until both containers were full; and (3) salt hydrate was intermittently removed from container 24.

EXAMPLE I

The solution in dissolver container 22 was heated to approximately thirty degrees centigrade and that in separation container 24 maintained at twenty degrees centigrade. The solutions circulated at approximately 100 grams per minute. The circulation continued for one hour.

At the end of the three and one half hour period, the concentration of the ethanol had increased from 10 to 20 percent. Approximately 63.69 grams of hydrated sodium sulfate were removed from 8,000 g initial solution. For two additional hours, 34.17 g hydrate was removed and the ethanol concentration of solution was increased to 33 percent.

EXAMPLE II

The solution in dissolver container 22 was heated to approximately thirty degrees centigrade and that in separation container 24 maintained at twenty degrees centigrade and the solutions circulated at approximately 100 grams per minute. The circulation continued for one hour.

At the end of the one hour period, the concentration of the ethanol had increased from 10 to 13 percent. Approximately 32.75 grams of hydrated sodium sulfate had been transferred from 8,000 g of initial solution. An additional two hours of operation improved ethanol concentration to 18 percent with the removal of 35.80 grams of hydrates. With additional removal of hydrates and at the end of a total 12 hour operation, a solution containing 46 percent ethanol was obtained.

EXAMPLE III

The solution in dissolver container 22 was heated to approximately thirty degrees centigrade and that in separation container 24 maintained at twenty degrees centigrade and the solutions circulated at approximately 100 grams per minute. The circulation continued for twelve hours with salt addition into the dissolver container 22 and hydrate removal from the separation container 24.

At the end of the twelve hour period the concentration of the ethanol had increased from 10 to 33 percent. Approximately 30.40 grams of hydrated sodium sulfate had been transferred to a beaker.

As can be understood from the above description, the technique of this invention has the advantages of removing large quantities of water with very little high-quality energy.

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A method of concentrating a dilute solution of ethanol in a sequence of stages in which the first stage comprises the steps of:

flowing said dilute solution of ethanol through a first container containing sodium sulfate;

maintaining the temperature of the first container at substantially thirty degrees centigrade while the dilute solution flows through it whereby said dilute solution dissolves the sodium sulfate;

flowing the dilute solution with the dissolved sodium sulfate into a second container;

maintaining the second container at substantially twenty degrees centigrade while the dilute solution flows through it, whereby the dissolved sodium sulfate precipitates out as hydrate crystals;

flowing the solution from the second container to the first container whereby the solution is repeatedly circulated between the first and second containers and back to the first container; and said circulating between the first and second containers and back to the first container including repeated steps until a dilute solution of ethanol with an initial concentration less than 15 percent by weight of ethanol in water has been circulated between the first and second containers in said first stage until the ethanol concentration by weight is increased to a value in excess of 45 percent, whereby the ethanol is concentrated using low quality energy in the first stage of the sequence of stages.

2. A method according to claim 1 further including the steps of:

removing the crystals of sodium sulfate from the second container;

permitting the crystals of sodium sulfate from the second container to stand at room temperature, whereby said crystals are regenerated to the anhydrous state; and feeding the regenerated anhydrous sodium sulfate back into the first container.

3. A method of concentrating an aqueous solution containing an organic chemical comprising the steps of:

adding an anhydrous salt capable of hydrating to a hydrate having a ratio of molecular weight of the hydrate to the anhydrous salt in a range between one-to-one and three-to-one into a first container;

mixing the salt with an aqueous solution of the organic chemical in the first container at a first temperature no more than 15 degrees centigrade above room temperature in which the salt is soluble in that solution;

transferring the solution to a second container with cooling to a temperature substantially room temperature, whereby a hydrate of the salt is formed, and removing the hydrate of the salt from the second container.

4. A method according to claim 3 in which the step of removing the hydrate includes the step of maintaining the second container at a temperature at which the hydrate precipitates.

5. A method according to claim 4 in which the step of adding a salt includes the step of adding a non-toxic salt into the first container.

6. A method according to claim 3 in which the step of adding a salt includes the step of adding a non-toxic salt into the first container.

7. A method according to claim 6 in which the step of removing the hydrate includes the step of seeding the solution in the second container with a means for causing precipitation.

8. A method according to claim 3 in which the step of removing the hydrate includes the step of seeding the solution in the second container with a means for causing precipitation.

9. A method according to claim 8 in which the step of adding a salt includes the step of adding a non-toxic salt into the first container.

* * * * *